(12) United States Patent
Mauldin et al.

(10) Patent No.: US 10,517,741 B2
(45) Date of Patent: Dec. 31, 2019

(54) SURGICAL METHOD AND INSTRUMENTATION ASSEMBLY FOR POSITIONING AN ANKLE PROSTHESIS

(71) Applicant: Tornier, Inc., Bloomington, MN (US)

(72) Inventors: Richard Garret Mauldin, Erie, CO (US); Yann Brunnarius, Chatuzange le Goubet (FR); Delphine Henry, Saint-Ismier (FR)

(73) Assignee: Tornier, Inc., Bloomington, MN (US)

( * ) Notice: Subject to any disclaimer, the term of this patent is extended or adjusted under 35 U.S.C. 154(b) by 648 days.

(21) Appl. No.: 15/044,441

(22) Filed: Feb. 16, 2016

(65) Prior Publication Data

US 2016/0256293 A1    Sep. 8, 2016

Related U.S. Application Data

(60) Provisional application No. 62/129,593, filed on Mar. 6, 2015.

(51) Int. Cl.
*A61B 17/15* (2006.01)
*A61F 2/46* (2006.01)
*A61B 17/17* (2006.01)

(52) U.S. Cl.
CPC ............ *A61F 2/4606* (2013.01); *A61B 17/15* (2013.01); *A61B 17/1739* (2013.01);
(Continued)

(58) Field of Classification Search
CPC .... A61B 17/15; A61B 17/157; A61B 17/1775
See application file for complete search history.

(56) References Cited

U.S. PATENT DOCUMENTS

| 5,766,259 A | 6/1998 | Sammarco |
| 7,238,190 B2 * | 7/2007 | Schon ................. A61B 17/15 606/87 |

(Continued)

FOREIGN PATENT DOCUMENTS

| CA | 2 836 651 | 6/2014 |
| FR | 2 715 557 | 8/1995 |

(Continued)

OTHER PUBLICATIONS

Extended European Search Report in Application No. 18196933.8, dated Dec. 19, 2018 in 7 pages.
(Continued)

*Primary Examiner* — Anu Ramana
(74) *Attorney, Agent, or Firm* — Knobbe, Martens, Olson & Bear LLP

(57) ABSTRACT

This surgical ankle repair method comprises providing an instrumentation assembly for positioning an ankle prosthesis including a talar alignment instrument and a cutting block. The talar alignment instrument is positioned such that fins of the talar alignment instrument are disposed in gutters that extend below the tibia and around the trochlea of the talus. The talar alignment instrument is aligned so that the fins are parallel to the rotational plane of the talus. Alignment of the reference markers is confirmed. The talar alignment instrument is attached to the talus. The cutting block is fastened to the talar alignment instrument. The talus is rotated such that the tibial alignment structure is in a parallel alignment to the longitudinal axis of the tibia. The tibial alignment structure is attached to the tibia. A resection of the talus and at least one resection of the tibia is performed using the cutting block.

25 Claims, 13 Drawing Sheets

(52) U.S. Cl.
CPC ........ *A61F 2/4657* (2013.01); *A61B 17/1775* (2016.11); *A61F 2002/4623* (2013.01); *A61F 2002/4668* (2013.01)

(56) References Cited

U.S. PATENT DOCUMENTS

| | | | |
|---|---|---|---|
| 8,034,115 B2 | 10/2011 | Reiley | |
| 8,034,155 B2 | 10/2011 | Reiley | |
| 8,114,091 B2 * | 2/2012 | Ratron | A61B 17/15 606/86 R |
| 8,337,503 B2 | 12/2012 | Lian | |
| 8,475,463 B2 | 7/2013 | Lian | |
| 9,168,100 B2 * | 10/2015 | Hanson | A61B 17/1739 |
| 2007/0173947 A1 | 7/2007 | Ratron et al. | |
| 2012/0130434 A1 | 5/2012 | Stemniski | |
| 2013/0116797 A1 | 5/2013 | Coulange et al. | |
| 2015/0305753 A1 * | 10/2015 | McGinley | A61B 17/15 606/87 |

FOREIGN PATENT DOCUMENTS

| | | |
|---|---|---|
| WO | WO 2013/169475 | 11/2013 |
| WO | WO 2014/020561 | 2/2014 |
| WO | WO 2014/152535 | 9/2014 |

OTHER PUBLICATIONS

Extended European Search Report in Application No. 16158615.1, dated Jun. 20, 2016 in 7 pages.

* cited by examiner

SURGICAL METHOD AND INSTRUMENTATION ASSEMBLY FOR POSITIONING AN ANKLE PROSTHESIS

The present application claims priority to US. Provisional Application No. 62/129,593 filed Mar. 6, 2015 incorporated herein by reference.

The present invention concerns a surgical ankle repair method. The present invention also concerns a surgical instrumentation assembly for positioning an ankle prosthesis.

The ankle implants are generally positioned using the tibia as a reference, as disclosed in US-A-2013/0116797. A cutting block is attached to the tibia and aligned with the axis of the tibia, and resections of the talus are performed after having found the right foot position with respect to at least one rotational plane of the ankle.

The positioning of the resections of the talus may be challenging as the rotational plane of the talus is found by techniques whose accuracy can be improved. Inaccuracies in the positioning of the implants can result in excessive stresses on the bones and soft tissues around the implants, and may reduce longevity of the implants.

The aim of the invention is to provide a new surgical method which permits the physician to better position the prostheses with respect to the bones of the patient.

To this end, the invention concerns a surgical ankle repair method comprising the steps of:
   a) providing an instrumentation assembly for positioning an ankle prosthesis, the instrumentation assembly including a talar alignment instrument and a cutting block, the talar alignment instrument comprising a front portion and two fins extending from the ends of the front portion, said fins being adapted to be positioned in gutters extending below a tibia of a patient and around the trochlea of a talus of the patient, each fin including a reference marker, the cutting block comprising a tibial alignment structure and a recess which engages a protrusion provided on the talar alignment instrument,
   b) positioning the talar alignment instrument such that the fins are disposed in the gutters extending below the tibia and around the trochlea of the talus;
   c) aligning the talar alignment instrument so that the fins are parallel to the rotational plane of the talus, perpendicular to the rotational axis of the talus, and so that the reference markers are aligned with a longitudinal axis of the tibia;
   d) confirming alignment of the reference markers via imaging technology;
   e) mechanically attaching the talar alignment instrument to the talus;
   f) fastening the cutting block to the talar alignment instrument such that the recess engages the protrusion locked in a parallel orientation to the rotational plane of the talus;
   g) rotating the talus such that the tibial alignment structure is in a parallel alignment to the longitudinal axis of the tibia, thereby correcting any varus or valgus deformity of the talus;
   h) attaching the tibial alignment structure to the tibia; and
   i) performing a first resection of the talus and several resections of the tibia using the cutting block.

Thanks to the invention, the resections of the tibia and the talus are performed using the talus as reference, resulting in better alignment and positioning of the implants.

According to further aspects of the invention which are advantageous but not compulsory, such a surgical method may incorporate one or several of the following features:
   The imaging technology is selected from the group consisting of X-ray, CT, and MR imaging.
   The method comprises, after step i), a further step j) consisting in inserting, in at least one hole drilled in the talus at step e) for inserting screws adapted to mechanically attach the talar alignment instrument to the talus, a positioning element for positioning a cutting guide for performing a second resection of the talus.
   The at least one resection performed on the talus at step i) is a posterior chamfer, whereas at step j) the cutting guide for performing the second resection is also positioned against the posterior chamfer.
   The method comprises, after step j), a further step k) consisting in positioning, on the surface of the second resection, a cutting guide for performing a third resection of the talus, which forms with the second resection an anterior chamfer.
   The talar alignment instrument is used to align a second cutting guide for performing a second resection of the talus.
   The second cutting guide remains on the talus surface, the talar alignment instrument is removed and a third cutting guide is placed on the second cutting guide to perform a third resection of the talus which forms with the second resection an anterior chamfer.
   At least one hole drilled in the talus at step e) for inserting screws adapted to mechanically attach the talar alignment instrument to the talus is used for drilling a hole destined to receive an anchoring peg of a talus implant.
   The talar alignment instrument is mechanically attached to the talus using at least two screws.
   The reference markers for the fins mark a direction perpendicular of the fins.

The invention also concerns a surgical ankle replacement method comprising the steps of:
   a) placing a talar alignment instrument on the talus,
   b) positioning the talar alignment instrument on the talus
   c) aligning a reference marker provided on the talar alignment instrument
   d) mechanically attaching the talar alignment instrument to the talus,
   e) fastening a cutting block to the talar alignment instrument,
   f) locking a relative position of the cutting block and the tibia,
   g) performing, using the cutting block, at least one resection of a lower surface of the tibia and at least one resection of a top surface of the talus.

According to further aspects of the invention which are advantageous but not compulsory, such a surgical replacement method may incorporate one or both of the following features:
   At step b) the talon alignment instrument is positioned relative to a rational plane of the talus and to a rational axis of the talus.
   At step c) the reference marker allows matching of the instrument's axis and radii to the talus's radii and axis.

The invention also concerns a surgical instrumentation assembly for positioning an ankle prosthesis, the ankle prosthesis including a tibia implant and a talus implant, wherein the instrumentation assembly comprises:
   a talar alignment instrument adapted to be placed on a talus of a patient, and relative to the rotational plane of the talus, and centered on the rotational axis of the talus, and perpendicular to the rotational plane of the talus and mechanically attached to the talus, a cutting block adapted to be fastened to the talar alignment instrument and locked with respect to the tibia.

According to further aspects of the invention which are advantageous but not compulsory, such a surgical instrumentation assembly may incorporate one or several of the following features:

The talar alignment instrument comprises a front portion and two fins extending from the ends of the front portion, said fins being adapted to be positioned in gutters extending below the tibia and around the trochlea of the talus.

The front portion comprises holes for inserting screws for mechanically attaching the talar alignment instrument to the talus.

The front portion comprises a protruding portion adapted to be received in a recess of the cutting block, the recess and the protruding portion being configured to prevent relative displacement of the talar alignment instrument and the cutting block, and locking parallel to the rotational plane of the talus.

The recess and the protruding portion are complementary shaped.

The fins of the talar alignment instrument are provided with reference markers adapted to mark a direction perpendicular to the fins, and adapted to be aligned with the longitudinal axis of the tibia, and aligned to the rotational axis of the talus.

The reference markers are elongated slots.

The cutting block comprises a tibial alignment structure adapted to be aligned with the longitudinal axis of the tibia and mechanically attached to the tibia.

The cutting block is configured to permit the cutting of at least one surface or hole on the top surface of the talus and cutting of at least one surface or hole in the distal portion of the tibia.

The assembly further comprises one or several cutting guides configured to permit the cutting of additional surfaces or holes on the top surface of the talus, whereas said cutting guides are adapted to be positioned against prior cut surfaces or holes.

At least one of the cutting guides for cutting additional surfaces or holes comprises at least one positioning shape adapted to be positioned against a screw inserted in a hole previously drilled in the talus for inserting a screw for mechanically attaching the talar alignment instrument to the talus.

At least one of the cutting guides for the cutting additional surfaces comprises of at least one positioning shape adapted to be positioned against the talar alignment instrument attached to the talus.

The invention will now be explained in reference to the following figures, as an illustrative example. In the annexed figures.

A surgical method and an instrumentation assembly are described below for replacing an ankle articulation on a patient, by implanting tibia and talus prostheses. The method and the instruments described below can be used for implanting ankle prostheses having a wide variety of structures, for example having tibia and/or talus implants that are constituted by a plurality of parts assembled to one another, and that may be made of metal, polymer, ceramic, composite, and a variety of other materials.

For convenience, the description below describes directions relative to the bones of an ankle in their anatomical position, the terms posterior or rear, anterior, front, right, left, upper, lower, etc. should be understood relative to the ankle of a patient standing on a substantially horizontal surface and viewed from the ankle.

Initially, the bones of the ankle of the patient which include a talus T and a tibia B, need to be prepared by performing resections for receiving the implants.

Figure 1:
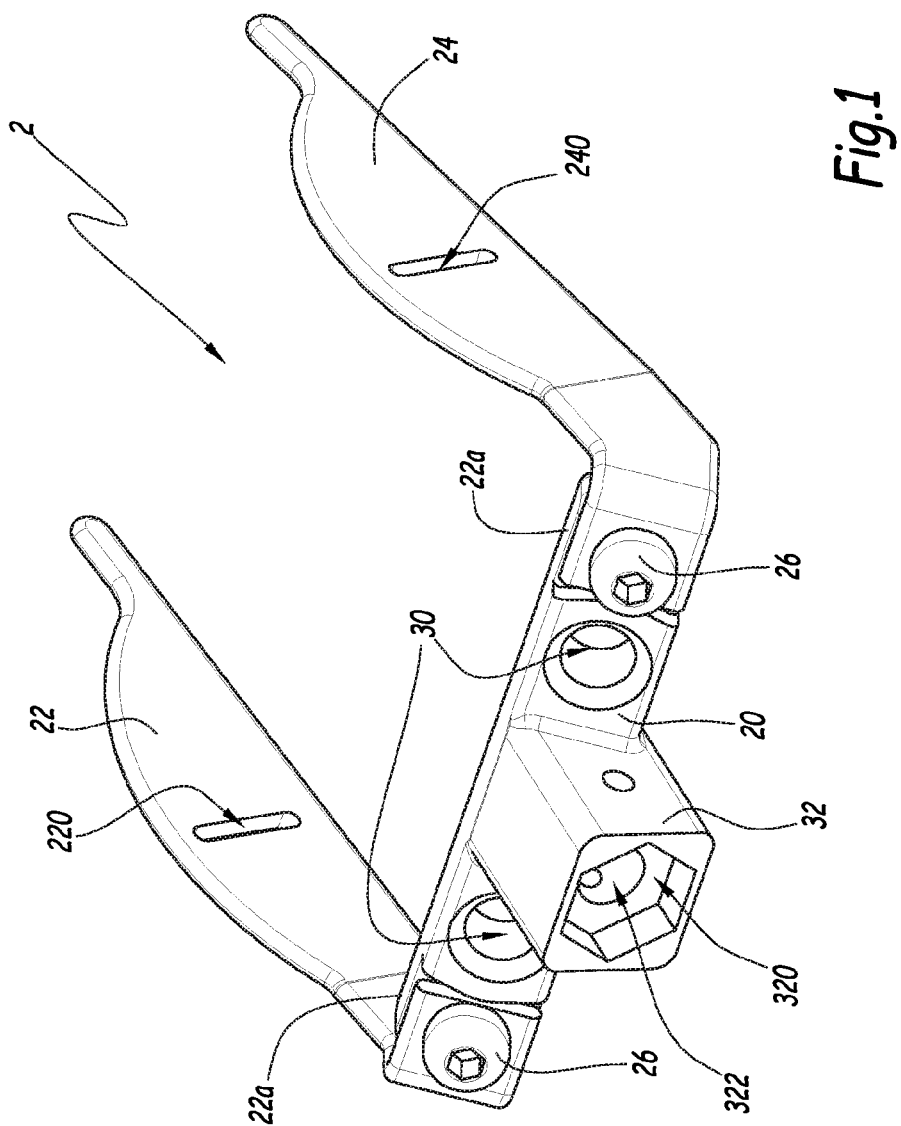
FIG. 1 is a perspective view of a talar alignment instrument belonging to an instrumentation assembly according to the invention.
Figure 2:
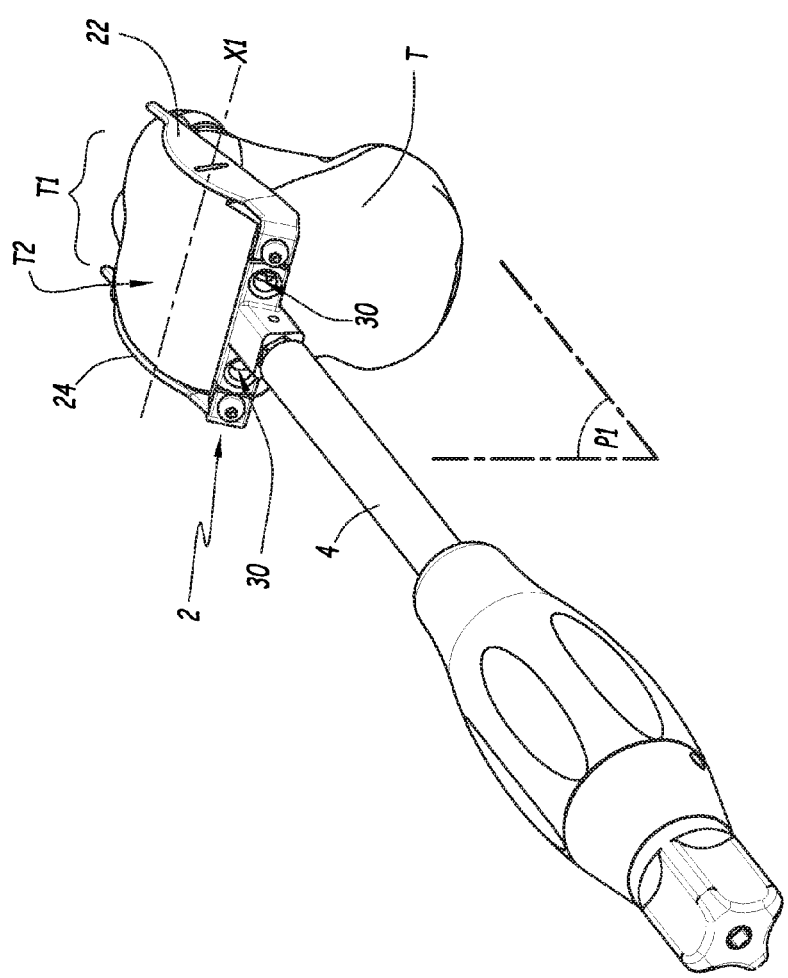
FIG. 2 is a perspective view of the positioning of the talar alignment instrument of FIG. 1 on a talus.

The instrumentation assembly comprises a talar alignment instrument 2 represented in FIG. 1. This talar alignment instrument 2 is adapted to be placed on the talus T during a first step of the surgical method according to the invention. The talus alignment instrument 2 comprises a front portion 20 and two fins 22 and 24 extending from the lateral most portions or ends 22a of front portion 20 in a substantially perpendicular direction. In the example, the fins 22 and 24 are independent parts which are fixed to the front portion 20, for example, by screws 26. Advantageously, the fins 22 and 24 may be made of an elastic metal, such as nitinol, so as to provide a flexibility suitable for adaptation of the talar alignment instrument to various ankle anatomies.

The resections performed on the talus T and the tibia B are performed using as a reference the talar alignment instrument 2, which is fixed to the talus T and positioned with respect to the rotational plane P1, and the talus T. The rotational plane P1 is best defined by the interface between the tibia, fibula, and talus. Since the tibia and fibular share this interface, the talus is the singular bone that best defines this surface. This part of the talus is called the trochlea, and where the talar alignment instrument directly attaches. This permits to provide better accuracy for the positioning of the implants and therefore to obtain a better comfort for the patient and a longer longevity of the implants.

The use of the talus T as reference for the bone resections also permits to determine the size of the implants. The trochlea of the talus as described above, also defines the width of the implant. Since the talar alignment instrument attaches directly to the trochlea, the width is determined accurately and therefore the size of the implant is accurately selected.

According to a non-shown embodiment, the talar alignment instrument 2 may be a monolithic or unitary structure, with the fins 22 and 24 and front portion 20 comprising 1 piece.

The fins 22 and 24 are adapted to be positioned in gutters G1 and G2 of talus T which extend around a trochlea T1 of the talus T, which is a globally cylindrical portion of the talus T. The gutters G1 and G2 extend below a portion of a tibia B and a portion of a fibula F. The gutter G1 is the vertical joint spaces comprised of the lateral side of the trochlea and inner side of the fibula. The gutter G2 is the vertical joint space comprised of the medial side of the trochlea and inner side of tibia's medial malleolus. The tibia B, the fibula F and the talus T together form the ankle articulation of a patient.

A second step of the surgical method consists in positioning the talus alignment instrument 2 so that the fins 22 and 24 are substantially parallel to a rotational plane P1 of the talus T. The rotational plane P1 is the plane defined by the rotation of the talus T with respect to the tibia B around a rotational axis X1 which is substantially parallel to a horizontal surface on which the patient is virtually standing, and which extends along a right-left direction of the ankle. The fins 22 and 24 have a substantially planar shape perpendicular to rotational axis X1. The fins 22 and 24 are also positioned in alignment of rotational axis X1.

Figure 3:
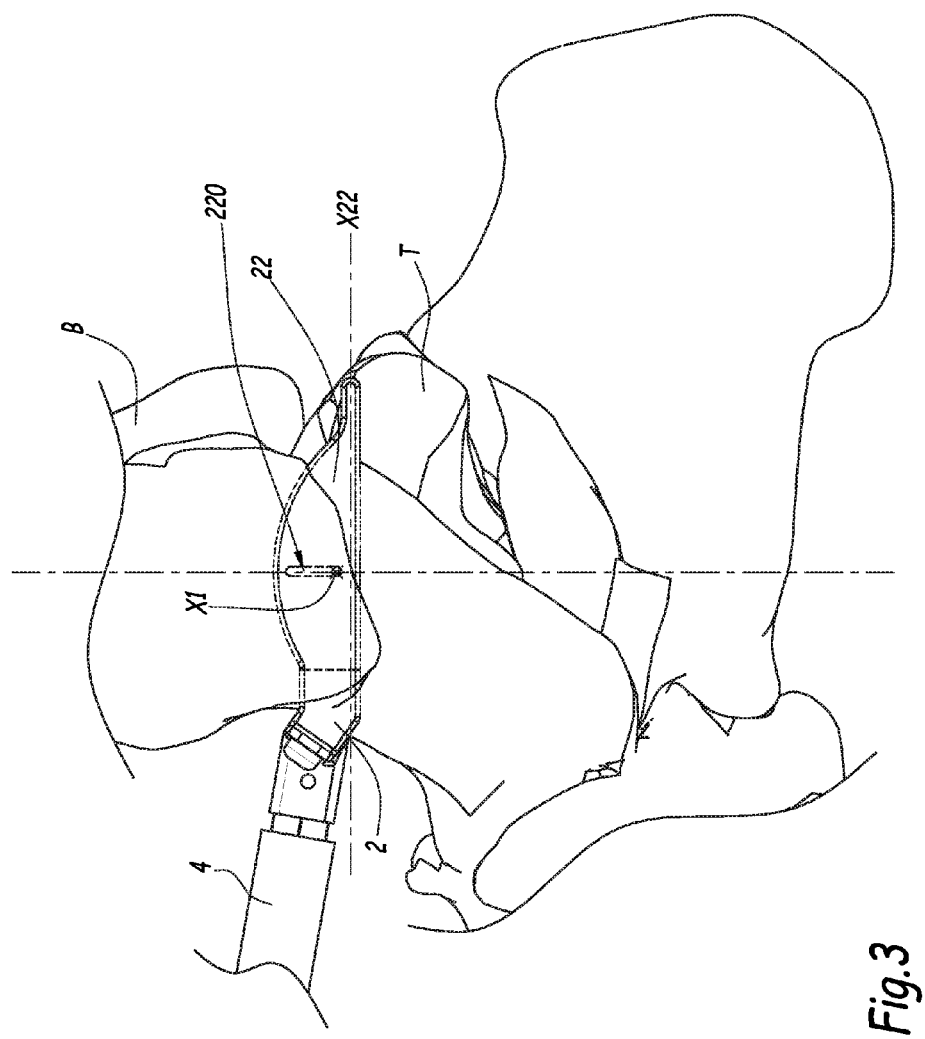
FIG. 3 is a side view of the positioning of the talar alignment instrument of FIG. 1 with respect to the talus and the tibia of a patient.
Figure 4:
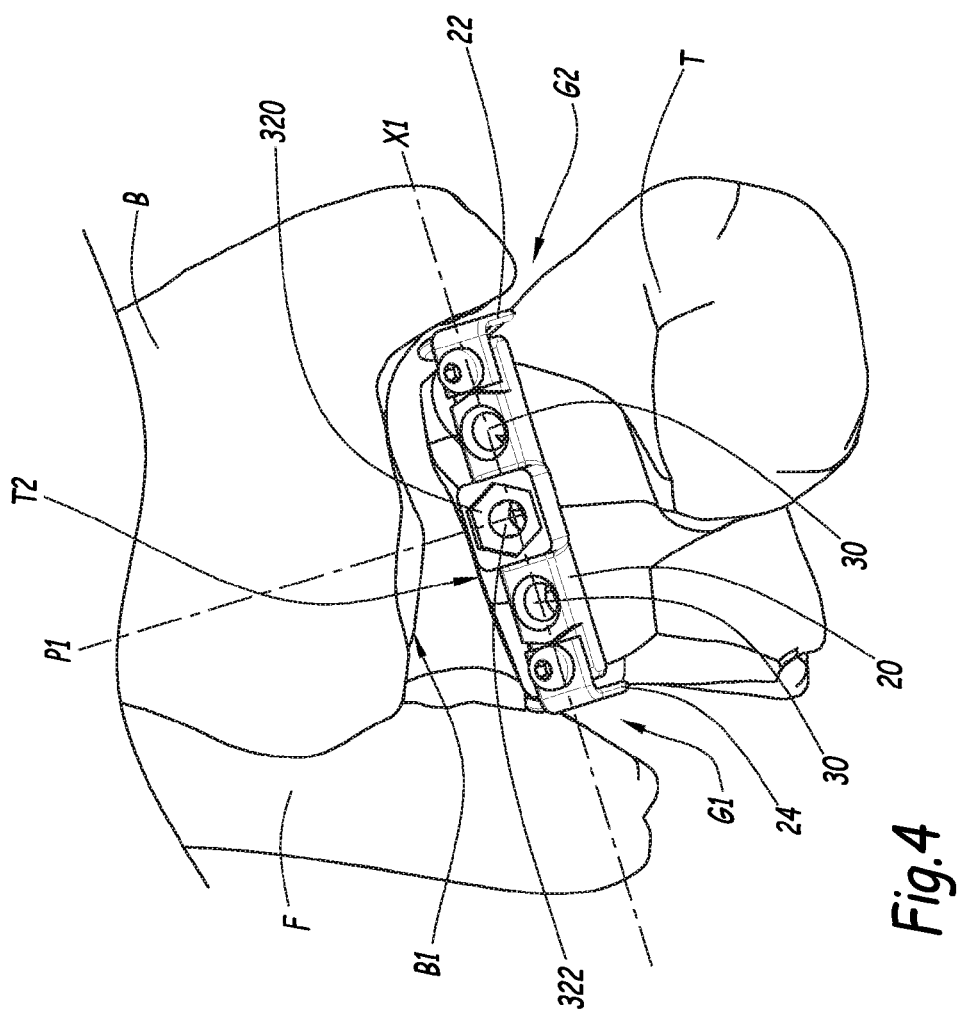
FIG. 4 is a front view of the positioning of the talar alignment instrument of FIG. 1 on a talus.

A further step of the surgical method, which is represented on FIG. 3, consists in aligning reference markers provided on the talar alignment instrument 2 with a longitudinal axis XB (illustrated in FIG. 6) of the tibia B. In the example shown, the reference markers are elongated slots, which may be holes 220 and 240 which are provided on fins 22 and 24 and adapted to mark a direction perpendicular to a longitudinal axis X22 of the fins 22 and 24. The alignment of the reference markers 220 and 240 is checked by imaging using for example X-rays, magnetic resonance imaging (MRI) or computed tomography (CT).

According to a non-shown embodiment, the reference markers may be other geometrically shaped holes allowing visualization and alignment utilizing, for example, X-rays, CT or MRI of the fins 22 and 24 to obtain perpendicular images to the talar alignment instrument 2. Alternatively, the reference markers may also be protrusions or recesses adapted to be visible in the above-mentioned imaging techniques.

Figure 8:
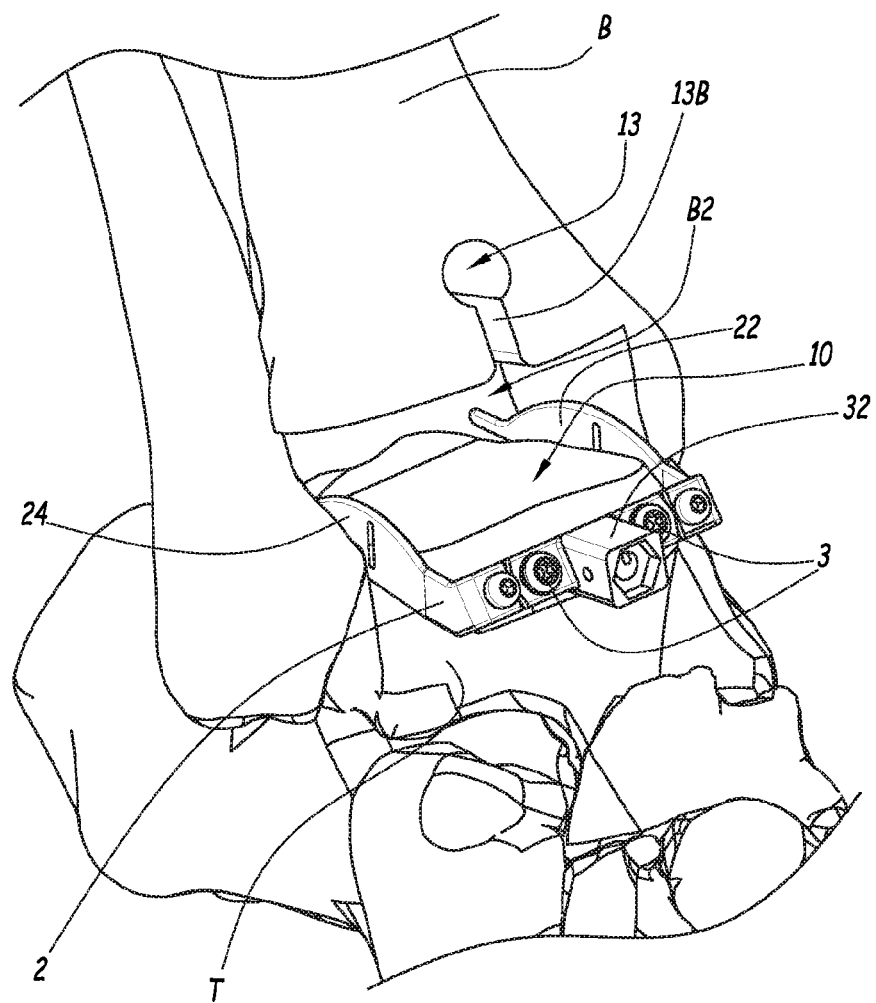
FIG. 8 is a perspective view of an ankle after resections have been performed.
Figure 9:
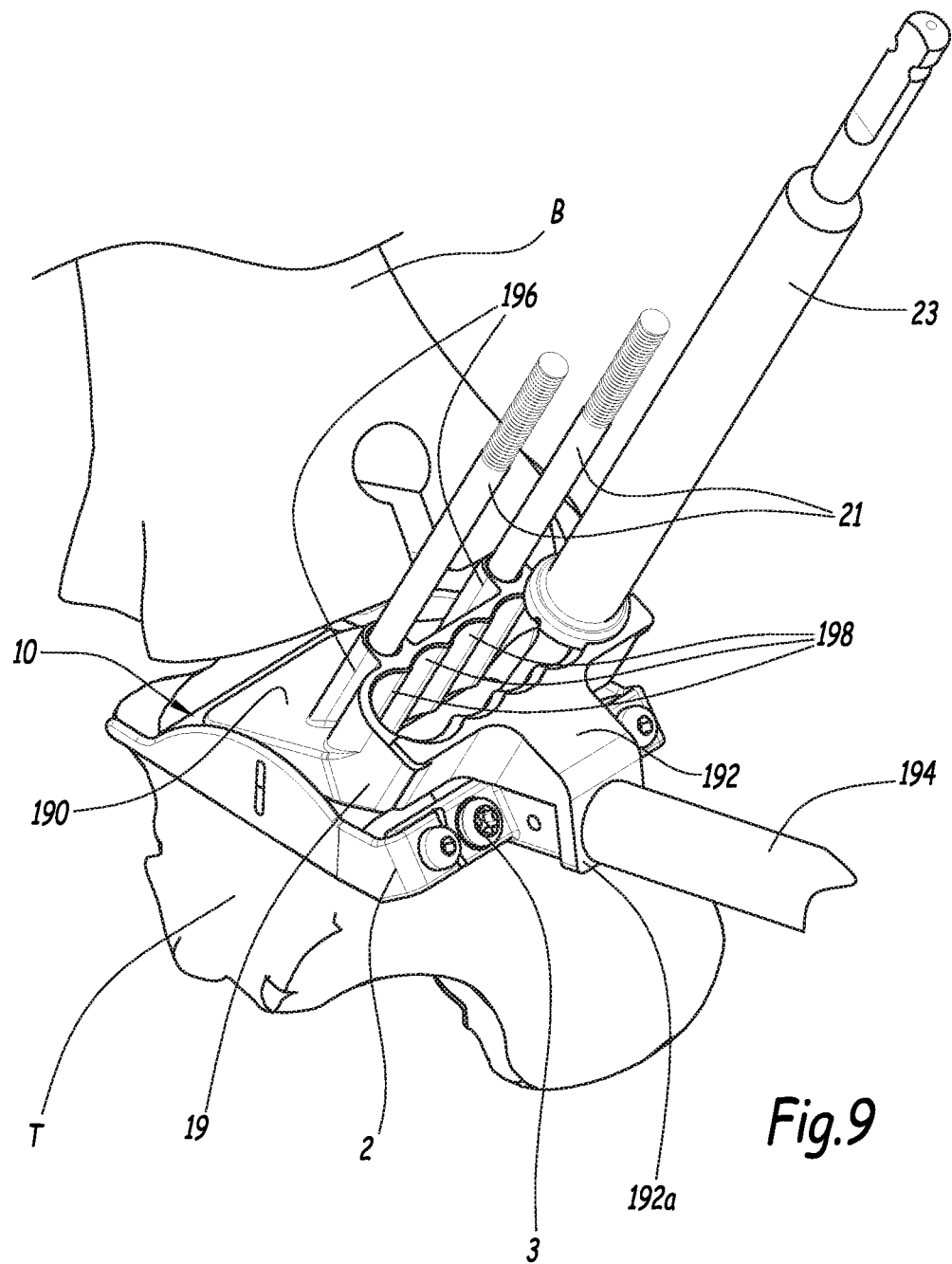
FIGS. 9 and 10 are perspective views similar to FIG. 8, during resection of other portions of the talus.

The talar alignment instrument 2 is then mechanically attached to the talus T, using at least two screws 3 represented on FIGS. 8 and 9. The screws 3 are inserted through holes 30 provided in the front portion 20 and in the holes drilled in the talus T.

During the positioning and attachment steps of the talar alignment instrument 2, the instrument 2 is handled or connected to a rod 4 having an end adapted to be inserted in a protruding portion 32 of front portion 20. The protruding portion 32 comprises an inner recess 320 having a hexagonal shape complementary with the distal end of the rod 4, which prevents rotation of the instrument 2 around the longitudinal axis of the rod 4.

According to a non-shown embodiment of the invention, instead of having a hexagonal shape, the inner recess 320 may present any other different shape adapted to prevent relative rotation between the rod 4 and the talar alignment instrument 2, for example a square shape, an ovoid shape, etc.

Figure 5:
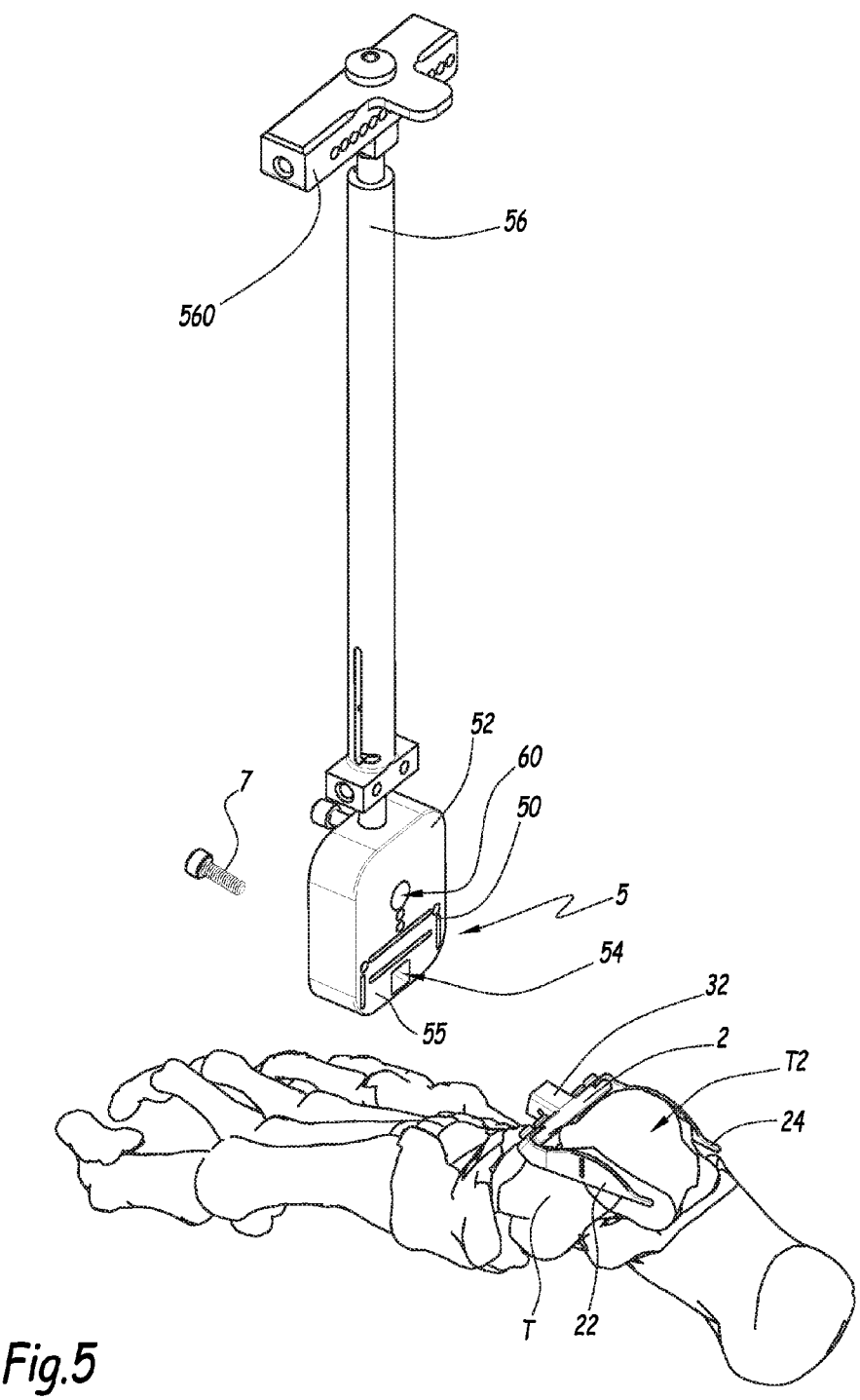
FIG. 5 is a perspective view of a cutting block belonging to an instrumentation assembly according to the invention and a talar alignment instrument positioned on a talus.

The instrumentation assembly also includes a cutting block 5, represented on FIG. 5. The cutting block 5 comprises slots 50 for passing cutting instruments which perform resections of a top surface T2 of the talus T and a lower surface B1 of the tibia B, as it will be described later.

The slots 50 are provided on a lower portion 55 of the cutting block 5. This lower portion 55 also includes a recess 54 adapted to receive the protruding portion 32 of the talar alignment instrument 2. The recess 54 and the protruding portion 32 are therefore complementary shaped in order to prevent relative rotation between the cutting block 5 and the talar alignment instrument 2. In the example, recess 54 and protruding portion 32 have a parallelepiped shape. In a non-shown embodiment, the shape of recess 54 and protruding portion 32 may be of any other shape adapted to prevent relative rotation.

The cutting block 5 also includes a tibial alignment structure 56 which extends substantially vertically from an upper portion 52 of the cutting block 5. The tibial alignment structure 56 is terminated by an upper alignment device 560.

In a further step, the cutting block 5 is attached to the talar alignment instrument 2 by mounting the recess 54 on the protruding portion 32 and by inserting a screw 7 through the recess 54 and in a threaded bore 322 provided in protruding portion 32.

Figure 6:
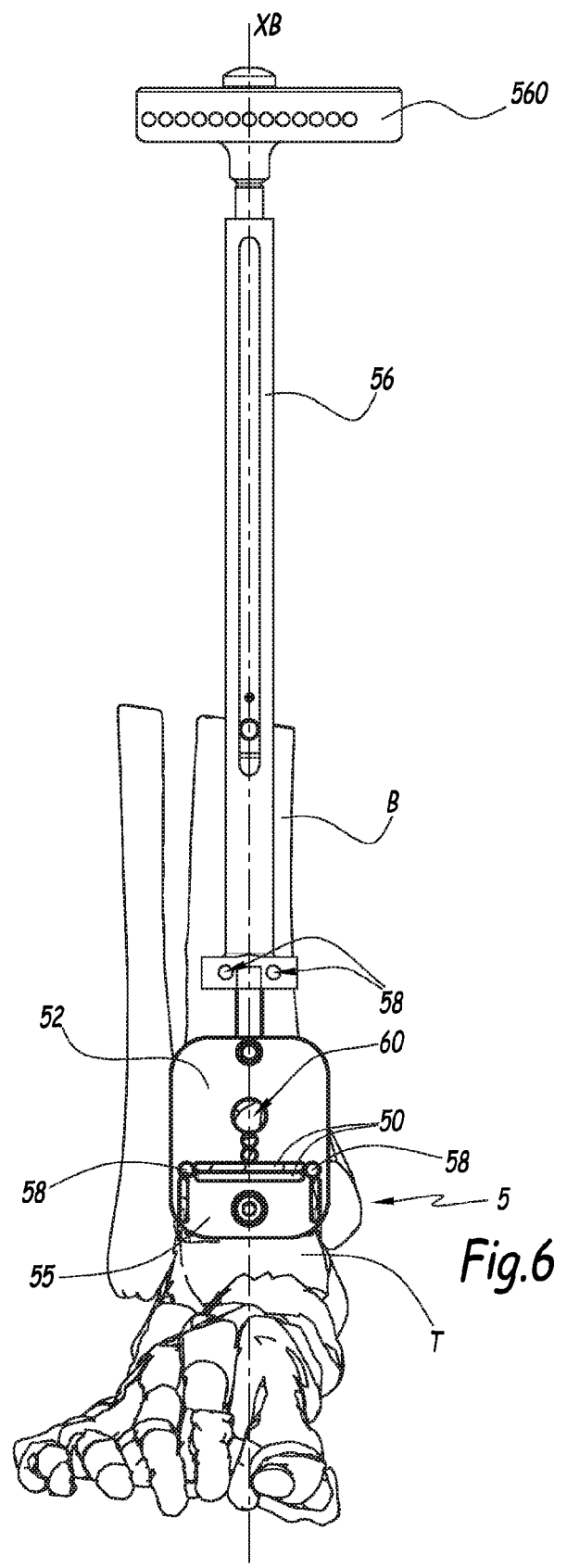
FIG. 6 is a front view of the cutting block of FIG. 5 positioned with respect to a talus and a tibia.

Once the cutting block 5 is fastened to the talar alignment instrument 2, the talus T is rotated with respect to the tibia B by moving the foot of the patient so that the tibial alignment structure 56 is in parallel alignment to the longitudinal axis XB of the tibia B, as shown on FIG. 6. In this step, the talus T is rotated in a plane perpendicular to the rotational plane P1 and comprising the longitudinal axis XB. By aligning the tibial alignment structure 56 with the longitudinal axis XB, varus or valgus deformities of the talus T are corrected.

Figure 7:
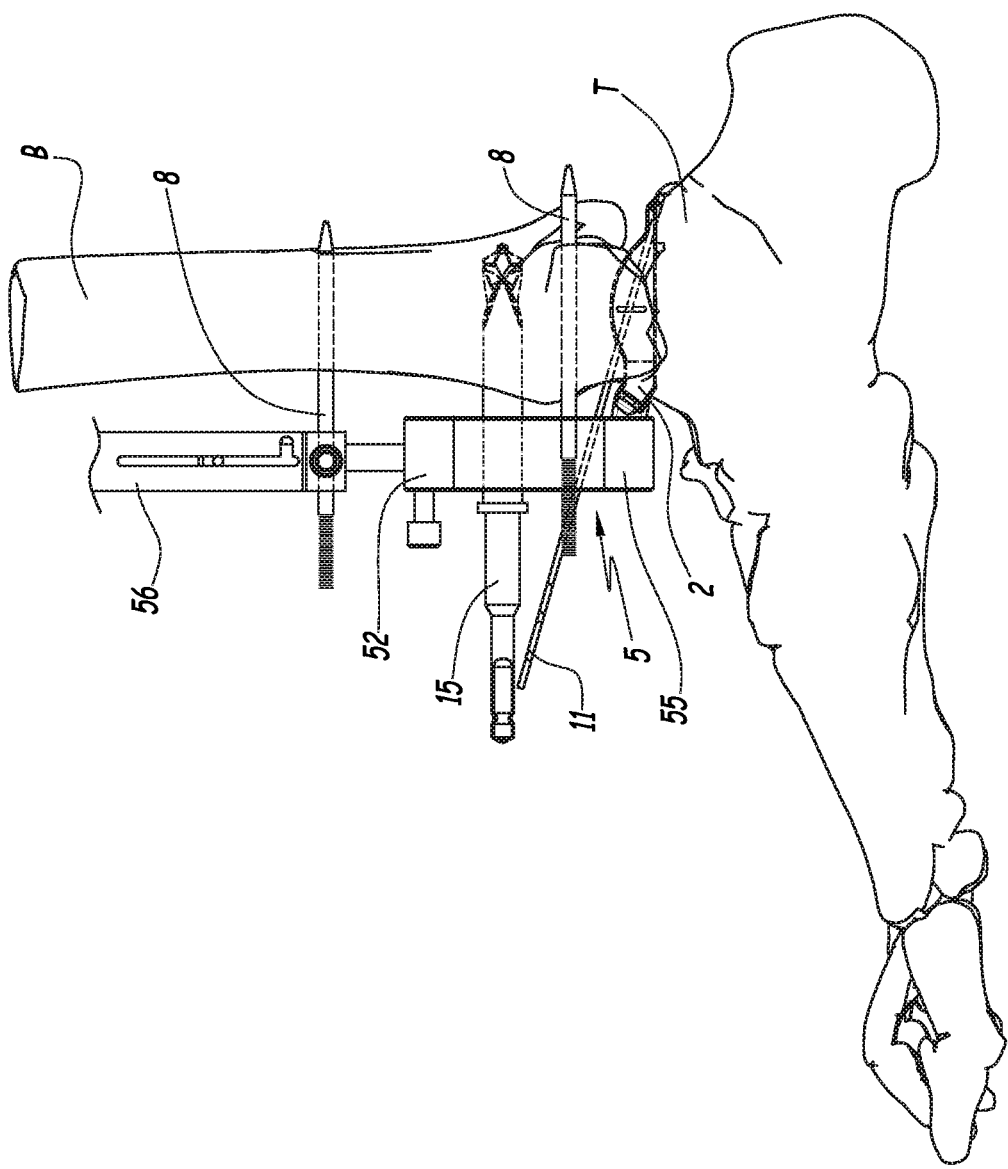
FIG. 7 is a side view of the talar alignment instrument and the cutting block during cutting of resections of the tibia and the talus.

Following the varus or valgus deformities correction, the cutting block 5 and the tibia B are mechanically attached so that the relative position of the talus T and the tibia B is locked in the subsequent steps of the surgical method. Several holes are drilled in the tibia B using drilling guides 58 provided on the lower portion 55 and on the tibial alignment structure 56. Pins 8 are inserted into the drilling guides 58 and in the holes drilled in the tibia B, as shown on FIG. 7, so that the cutting block 5 cannot move with respect to the tibia B. The alignment device 560 is also attached to a non-shown upper portion of the tibia B using non-shown attaching means.

Once the cutting block 5 is fixed with respect to the talus T and the tibia B, resections of the talus T and the tibia B can be performed so as to prepare the bones of the patient for the mounting of the ankle replacement implants. A top portion of the talus T is resected by cutting a posterior chamfer 10 represented on FIG. 8. This resection is performed using a saw blade 11 inserted in an angled slot of lower portion 55.

As represented on FIG. 8, resections of the lower surface B1 of the tibia B are performed by non-shown cutting blades, so as to form a square-shaped lodgment B2 comprising flat surfaces adapted to receive a tibial implant. A cylindrical recess 13 is drilled in the tibia B using a drill bit 15 inserted into a drilling guide 60 of cutting block 5. The recess 13 is destined to receive an anchoring keel of a tibial implant. A vertical hole 13B is also cut for linking the cylindrical recess 13 to the outer resected surface of the lodgment B2. The cutting block 5 is then removed. It should be noted that no additional holes are required to attach the cutting block to the talus, which may be referred to as "bonus holes". In reducing the number of holes created in the bone, bone loss is minimized.

Figure 12:
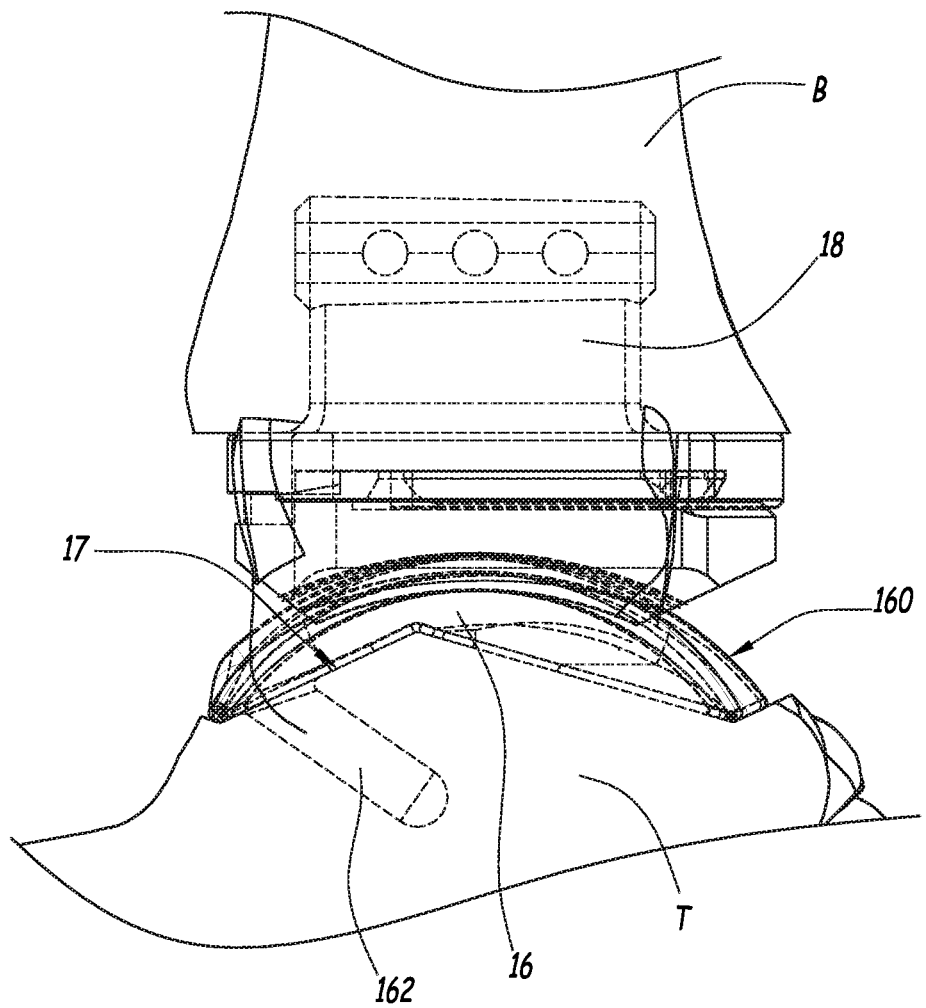
FIG. 12 is a side view of the ankle articulation, tibia and talus implants of FIG. 11.
Figure 13:
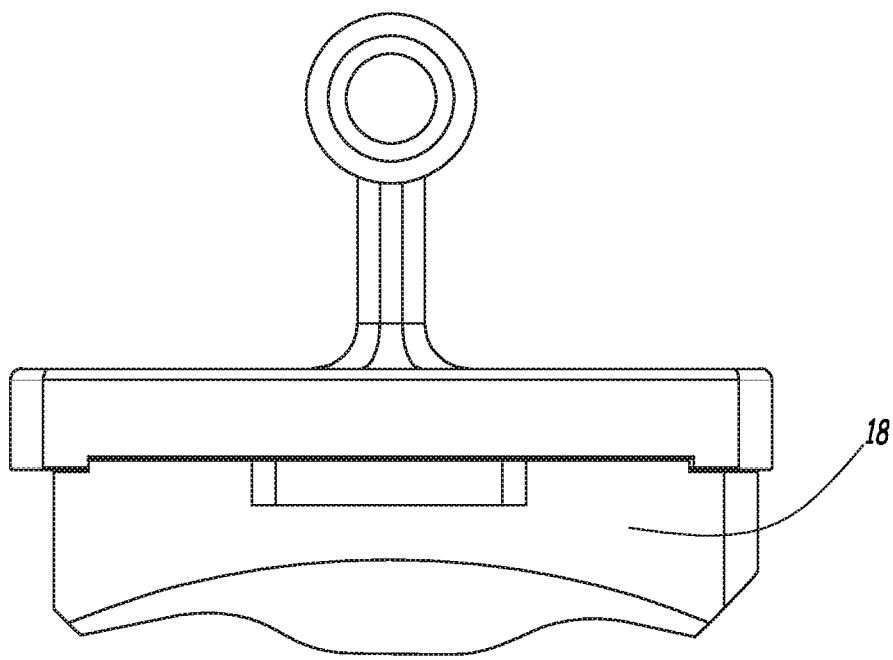
FIG. 13 is a view similar to FIG. 11 showing only the tibial implant.

In a further step of the surgical method, an anterior chamfer 17 is resected on the top surface of the talus T. This anterior chamfer 17, which is visible on FIG. 12, is obtained in two consecutive operations, shown in FIGS. 9 and 10.

In FIG. 9, a second cutting guide 19 of the instrumentation assembly, comprising a backwards extending portion 190 having a planar lower surface, is positioned against the posterior chamfer 10. The second cutting guide 19 also includes a front portion 192 which comprises a plate 192a adapted to be positioned against protruding portion 32 thanks to non-shown complementary shaped surfaces. The front portion 192 is extended by a rod 194 for handling the cutting guide 19.

As an optional feature, the second cutting guide 19 comprises two lodgments 196 which define cylindrical slots for passing two pins 21, which are inserted in non-shown holes drilled in the talus T. The pins 21 permit to further lock the position of the second cutting guide 19 with respect to the talus T.

Figure 10:
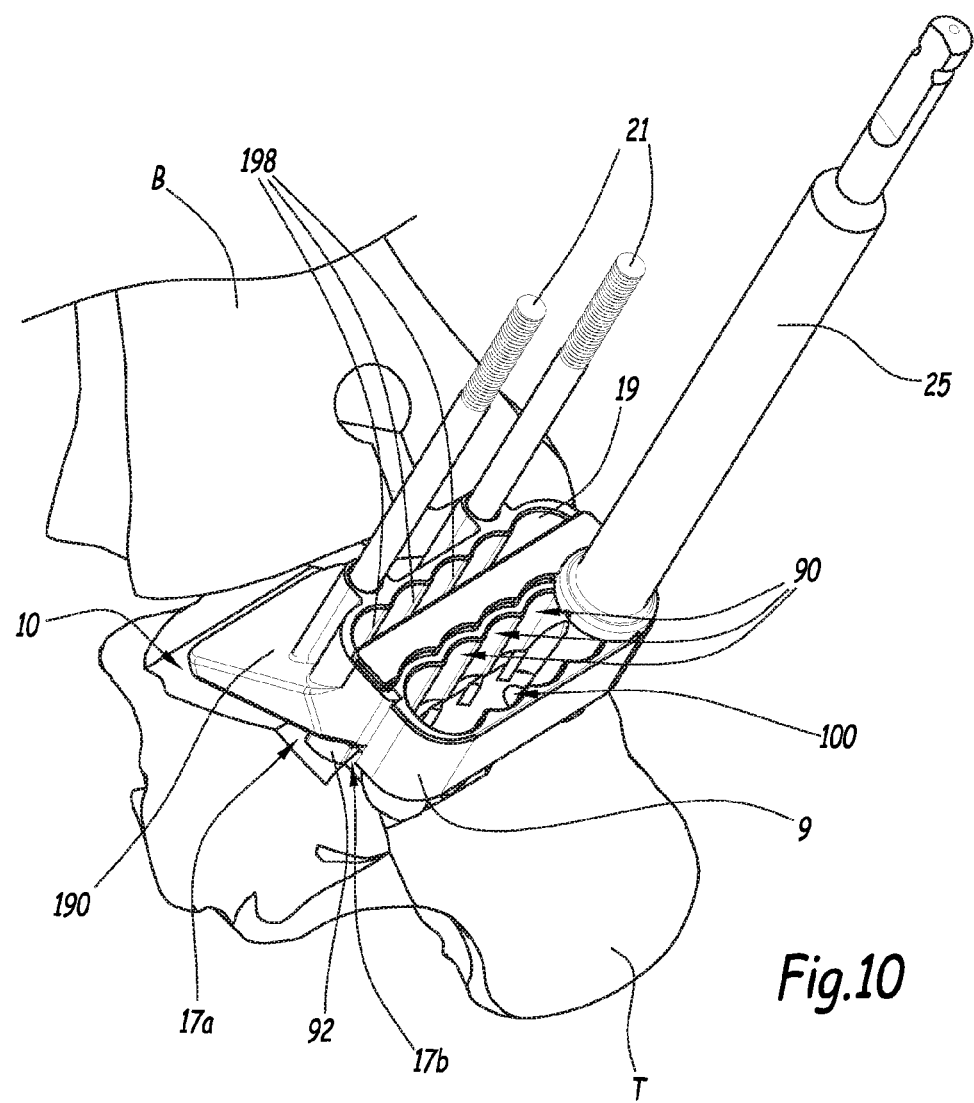

The second cutting guide 19 comprises several cylindrically shaped lodgments 198 adapted to receive a drilling bit 23 used to cut a first portion 17a, visible on FIG. 10 of the anterior chamfer 17. As shown on FIG. 9, the first portion 17a of the anterior chamfer 17 is obtained by five adjacent consecutive drilling operations. As an alternative, the first portion 17a of the anterior chamfer 17 may be obtained using different drilling or cutting means.

On FIG. 10, a second portion 17b of the anterior chamfer 17 is resected. During this operation, the second cutting guide 19 is kept into place, the talar alignment instrument 2 is dismounted, leaving open a hole 100 of the talus T, in which one of the screws 3 was present to attach the talar alignment instrument 2 to the talus T. The front portion 192 of the second cutting guide 19 is removable from a main portion of the second cutting guide 19, which comprises the lodgments 198. This front portion 192 is removed and replaced by a third cutting guide 9 of the instrumentation assembly. The third cutting guide 9 comprises five adjacent lodgments 90 adapted to receive a drilling bit 25, which could be the same as drilling bit 23, and which is adapted to drill the second portion 17b of the entire chamfer 17 in five drilling operations. The third cutting guide 9 also comprises, extending besides lodgments 90, a positioning block 92 adapted to be inserted in the lodgments 198 of the second cutting guide 19 to lock in position the third cutting guide 9 with respect to the second cutting guide 19. The positioning block 92 is inserted in the second cutting guide 19, a lower end of the positioning block 92 is in contact with the first portion 17a of the anterior chamfer 17.

Figure 11:
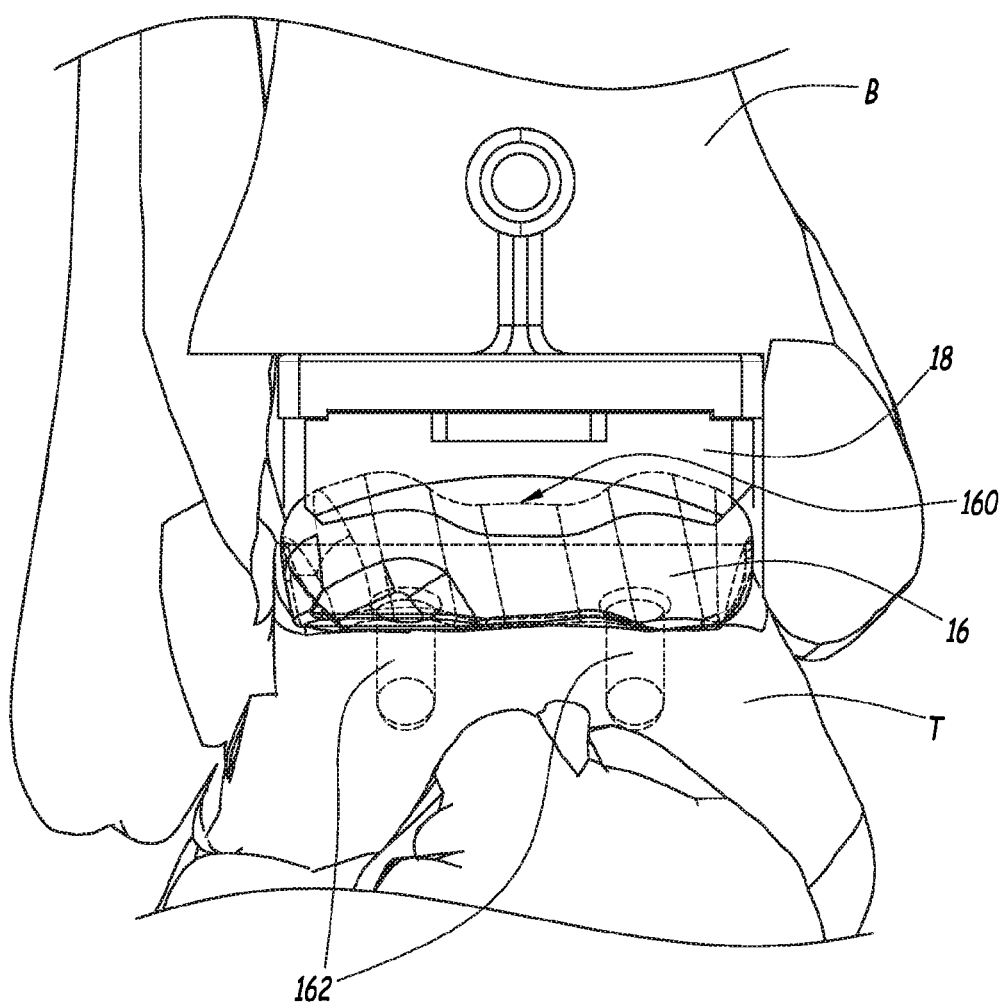
FIG. 11 is a front view of an ankle articulation equipped with tibia and talus implants shown in ghost lines.

When the second portion 17b is obtained, the resection of the anterior chamfer 17 is complete and a talus implant 16 can be mounted on the talus T, as shown on FIGS. 11 and 12. The talus implant 16 comprises an articulation surface 160, and two anchoring pegs 162, which are inserted in the holes 100 in which the screws 3 for fixing the talar alignment instrument 2 were inserted. The holes 100 may be prepared for the reception of the pegs 162 by a drilling at the diameter of the pegs 162.

A tibia implant 18 is inserted in the recess 13 prepared in the tibia B. Suitable tibia implants include, for example, Salto Talaris™ Total Ankle Prosthesis (manufactured by Tornier), INFINITY® total ankle system (manufactured by INBONE), Scandinavian Total Ankle Replacement (START™ Ankle) (manufactured by Stryker), Integra® Total Ankle Prosthesis (manufactured by Integra), Zenith™ Total Ankle Replacement (manufactured by Corin), BOX® Total Ankle Replacement (manufactured by MatOrtho®).

The holes 100 which are drilled for receiving screws 3 for attaching talus alignment instrument 2 to the talus T are used to receive anchoring pegs 162 of the talus implant 16. This permits the physician to reduce the number of holes drilled in the bones during the surgical procedure and which are left unused after the ankle replacement.

According to a non-shown embodiment of the invention, after the cutting of the posterior chamfer 10, the talar alignment instrument 2 may be removed. In such a case, the holes 30 of the front portion 20 may be provided with a lateral getaway formed by a slot so that the talar alignment instrument 2 can be removed without dismounting the screws 3, which are left inserted in the talus T.

To cut the first portion 17a of the anterior chamfer 17, a cutting guide similar to the cutting guide 19 is positioned against the screws 3 and against the posterior chamfer 10.

Once the first portion 17a is drilled, the cutting guide is removed and a second cutting guide is positioned against the posterior chamfer 10 and the first portion 17a of the anterior chamfer 17. The second portion 17b of the anterior chamfer 17 is then drilled.

Other embodiments are envisioned and within the scope of this application including patient specific instruments and implants. Ankle prosthesis instruments including tibial and talar guides may be prepared or manufactured based on patient specific anatomical data obtained using imaging technology including but not limited to X-ray, CT, and MRI imaging. In one embodiment, a physician may use anatomical imaging data of a patient and transmit this anatomical data to an instrument/implant manufacturer, wherein the instrument/implant manufacturer can create an instrument and/or implant which is designed based on the patient's specific anatomical data. Talar alignment instruments, cutting guides, cutting blocks, screws, and jigs may be manufactured with surfaces, angles, orientations, and structures which conform or complement the specific anatomy of the patient. For example, cutting guides having slots and (pin) holes for cutting the talus and aligning the ankle may include geometries conforming to anatomical surfaces or regions of the tibia, talus, other anatomical ankle bones, tendons, muscles, and markers.

In one particular embodiment, the talar alignment instrument 2 of the present disclosure may be created using patient specific anatomical data. More specifically, images of a patient may be obtained using MRI, X-ray, CT and combinations thereof. Images/scans may be represented as a virtual model of the patient's anatomy whereupon a physician may create and size patient specific implants and instruments. Alternatively images and/or scans of a patient's anatomy may be sent to an implant/instrument manufacturer whereupon a custom designed, or patient specific implant/instrument may be created. Specifically, scans of the hard and soft tissues can be used to create custom instrumentation, tools and implants for total ankle prostheses, including, but not limited to, talar alignment instruments, and cutting blocks and jigs having cutting slots and drill guides which are specific to the patient's anatomy/geometry. With regards to the current invention, the talar alignment instrument may include fins corresponding to patient anatomy including the gutters on the trochlea and taking into account any varus and valgus deformities.

In another embodiment, patient specific instruments/implants can be created by first taking into account a patient's corrected anatomy and then building the implants, instruments and tools to correspond to the corrected anatomy. In more detail, a surgeon can use patient anatomical images, such as x-ray and CT images and load those images into 3-D CAD software and correct a varus or valgus deformity first in a 3-D software, next a patient specific cutting jig or block is generated based on the corrected deformity. Once the block is manufactured, the surgeon may secure the patient specific block when the ankle is plantar flexed, enabling the surgeon to attach the patient specific cutting block to the talus only. The surgeon can correct the varus or valgus deformity by rotating the cutting block left and right, or medially and laterally. Next, the surgeon may then align the cutting block with the longitudinal axis of the tibia and place a pin in the tibia to attach the patient specific cutting block to the tibia. It should be noted that the aforementioned surgical steps are all performed while the ankle is plantar flexed, exposing maximum surface area of the talus to accurately position and attach the talus. The invention also concerns a kit for positioning an ankle prosthesis including a talar alignment instrument and a cutting block, the talar alignment instrument comprising a front portion and two fins extending from the ends of the front portion, said fins being adapted to be positioned in gutters extending below a tibia of a patient and around the trochlea of a talus of the patient, each fin including a reference marker of a direction perpendicular to the fins, the cutting block comprising a tibial alignment structure and a recess which engages a protrusion provided on the talar alignment instrument.

The invention also concerns a surgical ankle repair method comprising, before the step of providing an instrumentation assembly, a first step consisting in performing MRI, CT or X-ray imaging of the anatomy of a patient, and wherein the step of providing an instrumentation assembly is realized on the basis of the anatomical data of the patient provided by said imaging. More specifically, the imaging data may be used to design a talar alignment instrument adapted to be placed on a talus of a patient, and relative to the rotational plane of the talus, and centered on the rotational axis of the talus, and perpendicular to the rotational plane of the talus and mechanically attached to the talus, and a cutting block adapted to be fastened to the talar alignment instrument and locked with respect to the tibia.

In certain embodiments, the imaging data collected can be used by the surgeon in planning procedural steps, including, but not limited to, planning surgical cuts or bone and tissue resection.

The technical features of the above-described embodiment and variants can be combined to form new embodiments of the invention.

The invention claimed is:

1. A surgical ankle repair method comprising the steps of:
   a) providing an instrumentation assembly for positioning an ankle prosthesis, the instrumentation assembly including a talar alignment instrument and a cutting block, the talar alignment instrument comprising a front portion and two fins extending from the ends of the front portion, said fins being adapted to be positioned in gutters extending below a tibia of a patient and around a trochlea of a talus of the patient, each fin including a reference marker, the cutting block comprising a tibial alignment structure and a recess which engages a protrusion provided on the talar alignment instrument,
   b) positioning the talar alignment instrument such that the fins are disposed in the gutters extending below the tibia and around the trochlea of the talus;
   c) aligning the talar alignment instrument so that the fins are parallel to the rotational plane of the talus, perpendicular to the rotational axis of the talus, and so that the reference markers are aligned with a longitudinal axis of the tibia;
   d) confirming alignment of the reference markers via imaging technology;
   e) mechanically attaching the talar alignment instrument to the talus;
   f) fastening the cutting block to the talar alignment instrument such that the recess engages the protrusion locked in a parallel orientation to the rotational plane of the talus;
   g) rotating the talus such that the tibial alignment structure is in a parallel alignment to the longitudinal axis of the tibia, thereby correcting any varus or valgus deformity of the talus;
   h) attaching the tibial alignment structure to the tibia; and
   i) performing a first resection of the talus and at least one resection of the tibia using the cutting block.

2. The surgical method of claim 1, wherein the imaging technology is selected from the group consisting of X-ray, CT, and MR imaging.

3. The surgical method of claim 1, wherein step e) further comprises drilling at least one hole in the talus, the method further comprising, after step i), a further step j) of inserting, in the at least one hole drilled in the talus at step e), a positioning element for positioning a cutting guide for performing a second resection of the talus.

4. The surgical method of claim 3, wherein the at least one resection performed on the talus at step i) is a posterior chamfer, and wherein at step j) the cutting guide for performing the second resection is also positioned against the posterior chamfer.

5. The surgical method of claim 4, wherein the method comprises, after step j), a further step k) of positioning, on the surface of the second resection, a cutting guide for performing a third resection of the talus, which forms with the second resection an anterior chamfer.

6. The surgical method of claim 1, wherein the talar alignment instrument is used to align a second cutting guide for performing a second resection of the talus.

7. The surgical method of claim 6, wherein the second cutting guide remains on the talus surface, the talar alignment instrument is removed and a third cutting guide is placed on the second cutting guide to perform a third resection of the talus which forms with the second resection an anterior chamfer.

8. The surgical method of claim 1, wherein at least one hole drilled in the talus at step e) for inserting screws adapted to mechanically attach the talar alignment instrument to the talus is used for drilling a hole destined to receive an anchoring peg of a talus implant.

9. The surgical method of claim 1, wherein the talar alignment instrument is mechanically attached to the talus using at least two screws.

10. The surgical method of claim 1, wherein the reference markers of the fins mark a direction perpendicular to the fins.

11. A surgical ankle replacement method comprising the steps of:
   a) placing a talar alignment instrument on the talus,
   b) positioning the talar alignment instrument on the talus,
   c) aligning a reference marker provided on the talar alignment instrument with either or both of a rotational plane of the talus and a longitudinal axis of the tibia,
   d) mechanically attaching the talar alignment instrument to the talus,
   e) fastening a cutting block to the talar alignment instrument, f) locking a relative position of the cutting block and the tibia, g) performing, using the cutting block, at least one resection of a lower surface of the tibia and at least one resection of a top surface of the talus.

12. The surgical ankle replacement method of claim 11, wherein at step b) the talar alignment instrument is positioned relative to the rotational plane of the talus and to a rotational axis of the talus.

13. The surgical ankle replacement method of claim 11, wherein at step c) the reference marker allows alignment of the instrument's axis with the rotational plane of the talus and with the longitudinal axis of the tibia.

14. A surgical instrumentation assembly for positioning an ankle prosthesis, the ankle prosthesis including a tibia implant and a talus implant, wherein the instrumentation assembly comprises:
a talar alignment instrument adapted to be placed on a talus of a patient, and relative to the rotational plane of the talus, and centered on the rotational axis of the talus, and perpendicular to the rotational plane of the talus and configured to be directly mechanically attached to the talus,
a cutting block adapted to be fastened to the talar alignment instrument and locked with respect to a tibia of the patient.

15. The surgical instrumentation assembly of claim 14, wherein the talar alignment instrument comprises a front portion and two fins extending from the ends of the front portion, said fins being adapted to be positioned in gutters extending below the tibia and around a trochlea of the talus.

16. The surgical instrumentation assembly of claim 15, wherein the front portion comprises holes for inserting screws for mechanically attaching the talar alignment instrument to the talus.

17. The surgical instrumentation assembly of claim 15, wherein the front portion comprises a protruding portion adapted to be received in a recess of the cutting block, the recess and the protruding portion being configured to prevent relative displacement of the talar alignment instrument and the cutting block, and locking parallel to the rotational plane of the talus.

18. The surgical instrumentation assembly of claim 17, wherein the recess and the protruding portion are complementary shaped.

19. The surgical instrumentation assembly of claim 15, wherein the fins of the talar alignment instrument are provided with reference markers adapted to mark a direction perpendicular to the fins, and adapted to be aligned with the longitudinal axis of the tibia, and aligned to the rotational axis of the talus.

20. The surgical instrumentation assembly of claim 19, wherein the reference markers are elongated slots.

21. The surgical instrumentation assembly of claim 14, wherein the cutting block comprises a tibial alignment structure adapted to be aligned with the longitudinal axis of the tibia and mechanically attached to the tibia.

22. The surgical instrumentation assembly of claim 14, wherein the cutting block is configured to permit the cutting of at least one surface or hole on the top surface of the talus and cutting of at least one surface or hole in the distal portion of the tibia.

23. A system, comprising:
the surgical instrumentation assembly of claim 14;
a first cutting guide configured to be positioned against a posterior chamfer of the talus; and
a second cutting guide configured to be positioned against a portion of an anterior chamfer of the talus;
wherein one or both of the first cutting guide and the second cutting guide permit the cutting of additional surfaces or holes on the top surface of the talus.

24. The surgical instrumentation assembly of claim 23, wherein at least one of the cutting guides for cutting additional surfaces or holes comprises at least one positioning shape adapted to be positioned against a screw inserted in a hole previously drilled in the talus for inserting a screw for mechanically attaching the talar alignment instrument to the talus.

25. The surgical instrumentation assembly of claim 23, wherein at least one of the cutting guides for the cutting additional surfaces comprises of at least one positioning shape adapted to be positioned against the talar alignment instrument attached to the talus.

* * * * *